United States Patent
Pollner et al.

(10) Patent No.: US 9,677,122 B2
(45) Date of Patent: *Jun. 13, 2017

(54) INTEGRATED CAPTURE AND AMPLIFICATION OF TARGET NUCLEIC ACID FOR SEQUENCING

(71) Applicant: GEN-PROBE INCORPORATED, San Diego, CA (US)

(72) Inventors: Reinhold Pollner, San Diego, CA (US); Shyun-Shyun Lee, San Diego, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/018,240

(22) Filed: Feb. 8, 2016

(65) Prior Publication Data
US 2016/0177374 A1 Jun. 23, 2016

Related U.S. Application Data

(63) Continuation of application No. 13/879,572, filed as application No. PCT/US2011/058819 on Nov. 1, 2011, now Pat. No. 9,255,293.

(60) Provisional application No. 61/409,107, filed on Nov. 1, 2010.

(51) Int. Cl.
*C12P 19/34* (2006.01)
*C12Q 1/68* (2006.01)
*C12Q 1/70* (2006.01)

(52) U.S. Cl.
CPC ............ *C12Q 1/6806* (2013.01); *C12P 19/34* (2013.01); *C12Q 1/686* (2013.01); *C12Q 1/6834* (2013.01); *C12Q 1/6874* (2013.01); *C12Q 1/70* (2013.01)

(58) Field of Classification Search
USPC .............................................. 435/6.12, 91.2
See application file for complete search history.

(56) References Cited

U.S. PATENT DOCUMENTS 8,440,405 B2 * 5/2013 Fu .................. C12Q 1/6858
435/6.12
8,486,625 B2 * 7/2013 Gunderson .......... C12Q 1/6837
435/287.2

* cited by examiner

*Primary Examiner* — Kenneth Horlick
(74) *Attorney, Agent, or Firm* — Alston & Bird LLP

(57) ABSTRACT

The invention provides efficient methods of preparing a target nucleic acid in a form suitable for sequencing. The methods are particularly amenable for preparing high quality nucleic acids for massively parallel sequencing. The methods involve capturing a target nucleic acid from a sample and PCR amplification of the target nucleic acid. The target nucleic acid is captured by binding to a capture probe, which in turn binds to an immobilized probe. The immobilized probe is typically immobilized via a magnetic bead. The captured target nucleic acid is PCR amplified by thermocycling without prior dissociation of the target nucleic acid from the beads. The efficiency of the method lies in part in that both the capture and amplification steps are performed in a single vessel. The amplified nucleic acid can then be sequenced.

20 Claims, 3 Drawing Sheets

INTEGRATED CAPTURE AND AMPLIFICATION OF TARGET NUCLEIC ACID FOR SEQUENCING

CROSS-REFERENCE TO RELATED APPLICATION

The present application is a continuation of U.S. application Ser. No. 13/879,572, filed on Jul. 2, 2013 and now U.S. Pat. No. 9,255,293, which is a 371 national stage entry of international application number PCT/US11/58819, filed on Nov. 1, 2011, and which claims the benefit of filed U.S. application No. 61/409,107, filed on Nov. 1, 2010, each of which is incorporated by reference in its entirety for all purposes.

BACKGROUND

Over the last three decades there has been an enormous increase in efficiency and corresponding decrease in cost of nucleic acid sequencing techniques. Traditional techniques for sequencing DNA are the dideoxy termination method of Sanger (Sanger et al., PNAS USA, 74: 5463 (1977)) and the Maxam-Gilbert chemical degradation method (Maxam and Gilbert, PNAS USA, 74: 560 (1977)). Both methods deliver four samples with each sample containing a family of DNA strands in which all strands terminate in the same nucleotide. Ultrathin slab gel electrophoresis, or more recently capillary array electrophoresis is used to resolve the different length strands and to determine the nucleotide sequence, either by differentially tagging the strands of each sample before electrophoresis to indicate the terminal nucleotide, or by running the samples in different lanes of the gel or in different capillaries.

The concept of sequencing DNA by synthesis without using electrophoresis was first described by Hyman, Analytical Biochemistry, 174: 423 (1988) and involves detecting the identity of each nucleotide as it is incorporated into the growing strand of DNA in polymerase reaction. Such a scheme coupled with the chip format and laser-induced fluorescent detection markedly increases the throughput of DNA sequencing projects.

More recently several different formats of so-called next generation and third generation sequencing methods have been described that can sequence millions of target templates in parallel. Such methods are particularly useful when the target nucleic acid is a heterogeneous mixture of variants, such as is often the case in a sample from a patient infected with a virus, such as HIV. Among the many advantages, sequencing variants in parallel provides a profile of drug resistant mutations in the sample, even drug mutations present in relatively minor proportions within the sample.

Although next generation and third generation sequencing methods are much more efficient than Sanger or Maxam-Gilbert sequencing methods in the amount of sequence generated in terms of time or dollars, they are also dependent on having high quality nucleic acids to sequence. The presence of impurities cannot only cause problems with sequencing reactions but in the case of contamination by non-target nucleic acids provides misinformation into the system that then complicates or even makes impossible a proper interpretation of the resulting data. Misinformation includes false positive signals, loss of robustness and sensitivity in the assay, and ambiguous results.

SUMMARY

The invention provides methods of preparing a target nucleic acid for sequencing or other uses. The methods involve contacting a target nucleic acid with a capture probe and an immobilized probe, the capture probe comprising a first segment that binds to the target nucleic acid and a second segment that binds to the immobilized probe, wherein the target nucleic acid binds to the first segment of the capture probe, and the second segment of the capture probe binds to the target, thereby capturing the target nucleic acid; and performing a PCR amplification of the captured target nucleic acid without dissociation from the capture probe bound to the immobilized probe, wherein the PCR amplification is performed in the same vessel as the contacting step. The amplified target nucleic acid can then be sequenced. Optionally, the target nucleic acid is an RNA molecule and the PCR amplification is an RT-PCR amplification. In some methods, the target nucleic acid is a population of RNA molecules, and the RT-PCR amplification results in an amplified population of nucleic acids, which are sequenced in the sequencing step. Optionally, the target nucleic acid is a viral RNA population, which may include viral mRNA and/or viral genomic RNA. In some methods, the species of the viral RNA population differ from one another by mutations, which are identified by the sequencing step. The identified mutations can include at least one drug resistance mutation. In some methods, at least one identified mutation is present in less than 10% or 1% of molecules in the population of mRNA molecules. Examples of viral RNA populations include an HIV, HCV or HBV mRNA population from a patient sample.

In some such methods, the immobilized probe is immobilized via attachment to a magnetic bead. In some such methods, the concentration of immobilized probe linked to magnetic beads is 10-30 pg/ml, preferably 15-25 ng/ml. In some methods, the PCR involves thermocycling between temperature ranges having a high of 90-99° C., preferably 95° C., and having a low of 55-65° C., preferably 60° C. In some methods, the concentration of the capture probe is 0.2-0.8 pmol/ml, preferably 0.4-0.5 pmol/ml.

In some methods, the sequencing step sequences at least 75% of the length of the target nucleic acid. In some methods, the RT-PCR is performed with a pair of primers hybridizing to conserved regions of the target molecule or its complement and proximate to the ends of the target molecule so as to allow amplification of at least 75% of the target molecule. In some methods, the sequencing step is performed by a massively parallel sequencing technique and at least 100,000 molecules in the population of the target molecules are sequenced. In some methods, the target nucleic acid is present in a serum or plasma sample. In some methods, the serum or plasma sample is treated with detergent to release viral RNA. In some methods, the first segment includes a nucleic acid of at least 10 bases complementary to the target nucleic acid. In some methods, the first segment includes a nucleic acid of 10-30 bases complementary to the target nucleic acid. In some methods, the first segment is complementary to a conserved region of a viral RNA target. In some methods, the contacting is performed with a plurality of capture probes, the capture probes having the same second segment and different first segments, the different first segments being complementary to different conserved regions of a viral RNA target.

In some methods, the first segment binds non-specifically to the target nucleic acid. Optionally, the first segment includes a random sequence of nucleotides that binds non-specifically to the target nucleic acid.

In some methods, the second segment includes a nucleic acid of at least six bases complementary to a nucleic acid of at least six bases in the immobilized probe. Optionally, the second segment includes a nucleic acid of 10-30 bases complementary to a nucleic acid of 10-30 contiguous bases in the immobilized probe. Optionally, the nucleic acid of the second segment is a homopolymer and the nucleic acid of the immobilized probe constitute a complementary homopolymer. Optionally, the homopolymer of the second segment is poly-A and the homopolymer of the immobilized probed is poly-T or vice versa. In some methods, the second segment of the capture probe and the complementary segment of the immobilized probe are L-nucleic acids.

In some methods, the target nucleic acid is contacted with the capture probe and immobilized probe simultaneously. In some methods, the target nucleic acid is contacted with the capture probe before the immobilized probe. In some methods, the binding of the target nucleic acid to the capture probe occurs under first hybridization conditions and the binding of the capture probe to the immobilized probe occurs under second hybridization conditions and the first conditions are more stringent than the second conditions. In some methods, the first conditions are at a higher temperature than the second conditions. For example, the first conditions can include a temperature of 50-70° C. and the second conditions include room temperature.

In some methods, the sequencing is performed by single-molecule real-time sequencing. Some methods involve forming a circular template comprising the amplified target nucleic acid. Some methods generate a sequencing read containing multiple copies of the target nucleic acid.

BRIEF DESCRIPTION

FIG. 1 shows a 2% gel of the amplification products generated in integrated capture and amplification reactions from clinical samples. Lane 4: 1 kb marker. Lane 5: 100% heated HCV1a plasma. Lane 6: 100% HCV3b plasma. Lane 7: 90% heated HCV1a plasma +10% HCV3b plasma Lane 8: 99% heated HCV1a plasma +1% HCV3b plasma.

DEFINITIONS

Figure 1:
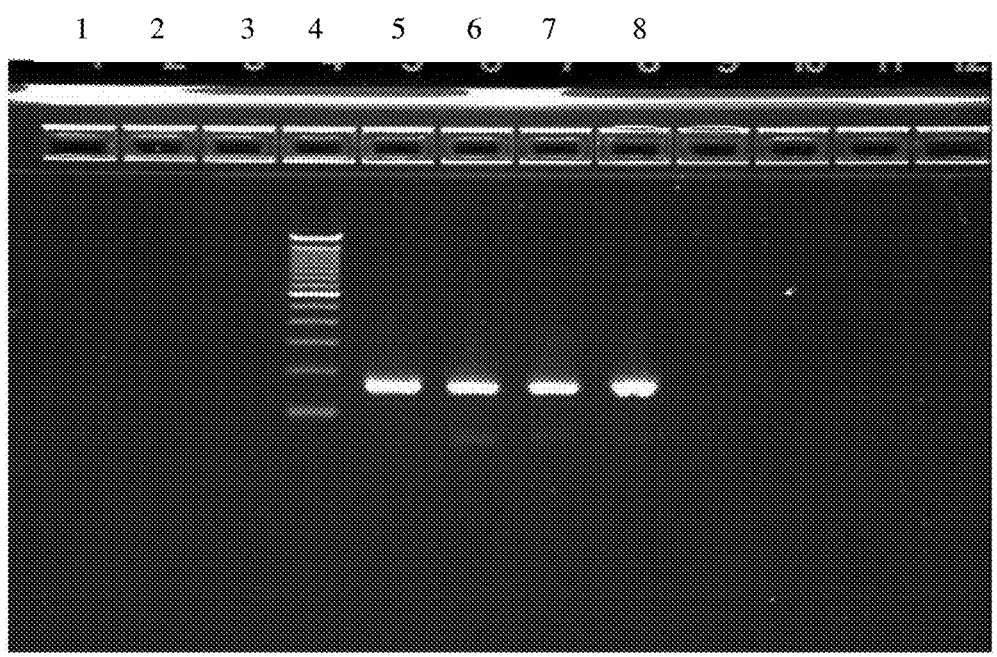

A nucleic acid refers to a multimeric compound comprising nucleotides or analogs that have nitrogenous heterocyclic bases or base analogs linked together to form a polymer, including conventional RNA, DNA, mixed RNA-DNA, and analogs thereof.

The nitrogenous heterocyclic bases can be referred to as nucleobases. Nucleobases can be conventional DNA or RNA bases (A, G, C, T, U), base analogs, e.g., inosine, 5-nitroindazole and others (The Biochemistry of the Nucleic Acids 5-36, Adams et al., ed., 11.sup.th ed., 1992; van Aerschott et al., 1995, Nucl. Acids Res. 23(21): 4363-70), imidazole-4-carboxamide (Nair et al., 2001, Nucleosides Nucleotides Nucl. Acids, 20(4-7):735-8), pyrimidine or purine derivatives, e.g., modified pyrimidine base 6H,8H-3,4-dihydropyrimidol[4,5-c[1,2]oxazin-7-one (sometimes designated "P" base that binds A or G) and modified purine base N6-methoxy-2,6-diaminopurine (sometimes designated "K" base that binds C or T), hypoxanthine (Hill et al., 1998, Proc. Natl. Acad. Sci. USA 95(8):4258-63, Lin and Brown, 1992, Nucl. Acids Res. 20(19):5149-52), 2-amino-7-deaza-adenine (which pairs with C and T; Okamoto et al., 2002, Bioorg. Med. Chem. Lett. 12(1):97-9), N-4-methyl deoxygaunosine, 4-ethyl-2'-deoxycytidine (Nguyen et al., 1998, Nucl. Acids Res. 26(18):4249-58), 4,6-difluorobenzimidazole and 2,4-difluorobenzene nucleoside analogues (Kiopffer & Engels, 2005, Nucleosides Nucleotides Nucl. Acids, 24(5-7) 651-4), pyrene-functionalized LNA nucleoside analogues (Babu & Wengel, 2001, Chem. Commun (Camb.) 20: 2114-5; Hrdlicka et al., 2005, J. Am. Chem. Soc. 127(38): 13293-9), deaza- or aza-modified purines and pyrimidines, pyrimidines with substituents at the 5 or 6 position and purines with substituents at the 2, 6 or 8 positions, 2-aminoadenine (nA), 2-thiouracil (sU), 2-amino-6-methylaminopurine, O-6-methylguanine, 4-thio-pyrimidines, 4-amino-pyrimidines, 4-dimethylhydrazine-pyrimidines, and O-4-alkyl-pyrimidines (U.S. Pat. No. 5,378,825; WO 93/13121; Gamper et al., 2004, Biochem. 43(31): 10224-36), and hydrophobic nucleobases that form duplex DNA without hydrogen bonding (Berger et al., 2000, Nucl. Acids Res. 28(15): 2911-4). Many derivatized and modified nucleobases or analogues are commercially available (e.g., Glen Research, Sterling, Va.).

A nucleobase unit attached to a sugar, can be referred to as a nucleobase unit, or monomer. Sugar moieties of a nucleic acid can be ribose, deoxyribose, or similar compounds, e.g., with 2' methoxy or 2' halide substitutions. Nucleotides and nucleosides are examples of nucleobase units.

The nucleobase units can be joined by a variety of linkages or conformations, including phosphodiester, phosphorothioate or methylphosphonate linkages, peptide-nucleic acid linkages (PNA; Nielsen et al., 1994, Bioconj. Chem. 5(1): 3-7; PCT No. WO 95/32305), and a locked nucleic acid (LNA) conformation in which nucleotide monomers with a bicyclic furanose unit are locked in an RNA mimicking sugar conformation (Vester et al., 2004, Biochemistry 43(42):13233-41; Hakansson & Wengel, 2001, Bioorg. Med. Chem. Lett. 11 (7):935-8), or combinations of such linkages in a nucleic acid strand. Nucleic acids may include one or more "abasic" residues, i.e., the backbone includes no nitrogenous base for one or more positions (U.S. Pat. No. 5,585,481).

A nucleic acid may include only conventional RNA or DNA sugars, bases and linkages, or may include both conventional components and substitutions (e.g., conventional RNA bases with 2'-O-methyl linkages, or a mixture of conventional bases and analogs). Inclusion of PNA, 2'-methoxy or 2'-fluoro substituted RNA, or structures that affect the overall charge, charge density, or steric associations of a hybridization complex, including oligomers that contain charged linkages (e.g., phosphorothioates) or neutral groups (e.g., methylphosphonates) may affect the stability of duplexes formed by nucleic acids.

Nucleic acids and their component nucleotides can exist in D or L form. The D-form is the natural form. An L-nucleic acid is the enantiomeric form of a D-nucleic acid. The source of stereoisomerism in a nucleic acid resides in the sugar moiety of each monomeric units forming the nucleic acid. Except for the stereoisomerisms at the sugar moiety of each monomeric unit, D and L-nucleic acids and their monomeric units are closely analogous. Thus, for example, the sugar moieties of an L-nucleic acid can be linked to the same nucleobases (i.e., adenine, guanine, cytosine, thymine and uracil) as occur in natural DNA or RNA, or any of the many known analogs of these nucleobases. The sugar moiety of L-nucleic acids can be ribose or deoxyribose or similar compounds (e.g., with 2'-methodyx or 2'halide substitutions). The sugar moieties can be linked by sugar phosphodiester linkages as in D-nucleic acids or by any of the analog linkages that have been used with D-nucleic acids, such as phosphorothioate or methylphosphonate linkages or peptide-nucleic acid linkages.

L-nucleotides incorporating at least the conventional nucleobases (i.e., A, C, G, T and U) are commercially available in the phosphoramidite form suitable for solid phase synthesis (e.g., ChemGenes Corporation (Wilmington, USA)). L-nucleic acids can be synthesized from L-nucleotides using the same solid phase synthesis procedures as are used for D-nucleic acids (e.g., an ABI synthesizer and standard synthesis protocols). L-nucleotides can also be linked to D-nucleotides by a conventional coupling cycle (see Hauser et al., Nucleic Acids Research, 2006, Vol. 34, No. 18 5101-5111 (2006), thus permitting synthesis of a chimeric nucleic acid having one segment in D-nucleic acid form and the other in L-nucleic form.

L-nucleic acids hybridize to one another according to analogous principles to D-nucleic acids (e.g., by formation of Watson-Crick or Hoogstein bonds) and have similar stability to hybrids of D-nucleic acids. The duplex formed from L-nucleic acids is a left-handed helix whereas that formed from D-nucleic acids is a right handed helix. Although L-nucleic acids can hybridize to each other, as further illustrated by the Examples, L-nucleic acids and particularly polyA or polyT L-nucleic acids have no ability to hybridize to a complementary segment of a poly A or polyT D-nucleic acid.

Unless otherwise apparent from the context, reference to a nucleic acid or nucleotide without specifying whether the form is D- or L-, includes either or both possibilities. However, the context may indicate that only a D nucleic acid or nucleotide is meant. For example, a nucleic acid occurring in nature would be understood to contain only D-nucleotides regardless whether so designated, as would a segment of a probe that forms a stable duplex with such a nucleic acid.

An oligomer may contain a "random polymer" sequence that refers to a population of oligomers that are substantially the same in overall length and other characteristics, but in which at least a portion of the oligomer is synthesized by random incorporation of different bases for a specified length, e.g., a random assortment of all four standard bases (A, T, G, and C) in a DNA oligomer, or a random assortment of a few bases (U and G) in a defined portion of a larger oligomer. The resulting oligomer is actually a population of oligomers whose finite number of members is determined by the length and number of bases making up the random portion (e.g., 2exp6 oligomers in a population of oligomers that contains a 6-nt random sequence synthesized by using 2 different bases).

Complementarity of nucleic acids means that a nucleotide sequence in one strand of nucleic acid, due to orientation of its nucleobase groups, hydrogen bonds to another sequence on an opposing nucleic acid strand. The complementary bases typically are, in DNA, A with T and C with G, and, in RNA, C with G, and U with A. Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm of hybridized strands, or by empirical determination of Tm by using routine methods. Tm refers to the temperature at which a population of hybridization complexes formed between two nucleic acid strands are 50% denatured. At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+0.41(% G+C), although other known Tm computations take into account nucleic acid structural characteristics.

"Hybridization condition" refers to the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other factors, such as the length of incubation time or reaction chamber dimensions may contribute to the environment (e.g., Sambrook et al., Molecular Cloning, A Laboratory Manual, 2.sup.nd ed., pp. 1.90-1.91, 9.47-9.51, 11.47-11.57 (Cold Spring Harbor Laboratory Press, Cold Spring Harbor, N.Y., 1989)).

Specific binding of a capture probe to a target nucleic or target nucleic acids means binding between a single defined sequence in the first segment of a capture probe and an exactly or substantially complementary segment on target nucleic acid(s) to form a stable duplex. Such binding is detectably stronger (higher signal or melting temperature) than binding to other nucleic acids in the sample lacking a segment exactly or substantially complementary to the single defined capture probe sequence. Non-specific binding of a capture probe to target nucleic acids means that the capture probe can bind to a population of target sequences that do not share a segment having exact or substantial complementarity to a single defined capture probe sequence. Such can be achieved by for example using a randomized sequence in the first segment of the capture probe.

Lack of binding between nucleic acids can be manifested by binding indistinguishable from nonspecific binding occurring between a randomly selected pair of nucleic acids lacking substantial complementarity but of the same lengths as the nucleic acids in question.

A "chimeric capture probe" serves to join a target nucleic acid and an immobilized probe by hybridization of complementary sequences. A chimeric target capture probe is sometimes referred to as a capture probe. A chimeric capture probe includes a first segment including a target-complementary region of sequence and a second segment for attaching the capture probe, or a hybridization complex that includes the capture probe, to an immobilized probe. The first segment can be configured to be substantially complementary to a specific target nucleic acid sequence so that a first segment and a target nucleic acid can hybridize to form a stable duplex (i.e., having a detectable melting point) under hybridizing conditions, such as described in the Examples. Alternatively, the first segment can be configured to nonspecifically bind to nucleic acid sequences in a sample under hybridizing conditions (see WO 2008/016988). The second segment includes a region of sequence that is complementary to a sequence of an immobilized probe. Preferably, a chimeric capture probe includes a nucleic acid homopolymer (e.g., poly-A or poly-T) that is covalently attached to the target-complementary region of the capture probe and that hybridizes under appropriate conditions to a complementary homopolymer of the immobilized probe (e.g., poly-T or poly-A, respectively) as previously described (U.S. Pat. No. 6,110,678 to Weisburg et al.). Capture probes may further comprise a third segment that acts as a closing sequence to inactivate unbound target capture probes in a capture reaction. This third segment can flank the first segment opposite the second segment (e.g., capture sequence:target hybridizing sequence:closing sequence) or it can flank the second segment opposite the first segment (e.g., closing sequence:capture sequence:target hybridizing sequence). See WO 2006/007567 and US 2009-0286249.

"Separating" or "isolating" or "purifying" refers to removing one or more components from a complex mixture, such as a sample. Preferably, a separating, isolating or purifying step removes at least 70%, preferably at least 90%, and more preferably about 95% of the target nucleic acids from other sample components. A separating, isolating or purifying step may optionally include additional washing steps to remove non-target sample components. It is understood that at least X % refers to a range from X % to 100% inclusive of all whole and partial numbers (e.g., 70%, 82.5%, and so forth.)

"Release" of a capture hybrid refers to separating one or more components of a capture hybrid from each other, such as separating a target nucleic acid from a capture probe, and/or a capture probe from an immobilized probe. Release of the target nucleic acid strand separates the target from other components of a capture hybrid and makes the target available for binding to a detection probe. Other components of the capture hybrid may remain bound, e.g., the capture probe strand to the immobilized probe on a capture support, without affecting target detection.

Reference to a range of value also includes integers within the range and subranges defined by integers in the range.

Transcription mediated amplification (TMA) is an isothermal nucleic-acid-based method that can amplify RNA or DNA targets a billion-fold in less than one hour's time. TMA technology uses two primers and two enzymes: RNA polymerase and reverse transcriptase. One primer contains a promoter sequence for RNA polymerase. In the first step of amplification, this primer hybridizes to the target RNA at a defined site. Reverse transcriptase creates a DNA copy of the target rRNA by extension from the 3' end of the promoter primer. The RNA in the resulting RNA:DNA duplex is degraded by the RNase activity of the reverse transcriptase. Next, a second primer binds to the DNA copy. A new strand of DNA is synthesized from the end of this primer by reverse transcriptase, creating a double-stranded DNA molecule. RNA polymerase recognizes the promoter sequence in the DNA template and initiates transcription. Each of the newly synthesized RNA amplicons reenters the TMA process and serves as a template for a new round of replication.

Reverse-transcriptase PCR (RT-PCR) includes three major steps. The first step is reverse transcription (RT), in which RNA is reverse transcribed to cDNA using reverse transcriptase. The RT step can be performed in the same tube with PCR (using a temperature between 40° C. and 50° C., depending on the properties of the reverse transcriptase used. The next step involves the denaturation of the dsDNA at temperature at or about 95° C., so that the two strands separate and the primers can bind again at lower temperatures and begin a new chain reaction. Then, the temperature is decreased until it reaches the annealing temperature which can vary depending on the set of primers used, their concentration, the probe and its concentration (if used), and the cations concentration. An annealing temperature about 5° C. below the lowest Tm of the pair of primers is usually used (e.g., at or around 60° C.). RT-PCR utilizes a pair of primers, which are respectively complementary to sequence on each of the two strands of the cDNA. The final step of PCR amplification is DNA extension from the primers with a DNA polymerase, preferably a thermostable taq polymerase, usually at or around 72° C., the temperature at which the enzyme works optimally. The length of the incubation at each temperature, the temperature alterations, and the number of cycles are controlled by a programmable thermal cycler.

Real-time polymerase chain reaction, also called quantitative real time polymerase chain reaction (Q-PCR/qPCR/qrt-PCR) or kinetic polymerase chain reaction (KPCR), is a laboratory technique based on the PCR, which is used to amplify and simultaneously quantify a targeted DNA molecule. It enables both detection and quantification (as absolute number of copies or relative amount when normalized to DNA input or additional normalizing genes) of one or more specific sequences in a DNA sample.

A copy of a target nucleic acid in a sequencing read means an identical copy or substantially identical copy (e.g., at least 80% sequence identity) differing as a result of nucleobase unit misincorporations in template-dependent extension or sequencing errors.

All temperatures are indicated in degrees Celsius.

DETAILED DESCRIPTION

I. General

The invention provides efficient methods of preparing a target nucleic acid in a form suitable for sequencing (although the target nucleic acid can also be used for other purposes, such as detection, quantification or other analysis). The methods are particularly amenable for preparing high quality nucleic acids for massively parallel sequencing. The methods involve capturing a target nucleic acid from a sample and PCR amplification of the target nucleic acid. The target nucleic acid is captured by binding to a capture probe, which in turn binds to an immobilized probe. The immobilized probe is typically immobilized via a magnetic bead. The captured target nucleic acid is PCR amplified without dissociating the target nucleic acids from the beads before performing the PCR. The efficiency of the method lies in part in that capture and amplification steps are fully integrated without eluting captured target from the magnetic beads before the amplification reaction is performed. The captured and amplified nucleic acid can then be further processed for sequencing. Although the principle of capturing a target nucleic acid via a capture probe and an immobilized probe is incorporated into the commercially available PROCLEIX® HIV-1/HCV Assay, its use in the present methods differs from such commercial use inter alia in that captured nucleic acids are amplified via reverse transcription and a thermocycling PCR reaction as distinct from isothermal transcription mediated amplification and the goal of preparation is sequencing of amplified target nucleic acids as distinct from simple detection.

II. Capture Probes

The invention employs chimeric target capture probes having at least first and second segments. The first segment binds to a target nucleic acid either specifically or nonspecifically (see U.S. Pat. No. 6,110,678 and WO 2008/016988). The second segment, sometimes known as a tail, binds to an immobilized probe and thus serves to capture the target nucleic bound to the capture probe to a support linked to an immobilized probe. Capture probes are typically provided in single-stranded form, or if not, are denatured to single-stranded form before or during use (see WO 2006/007567 and US 2009-0286249).

The first segment of the chimeric capture probe is typically designed to bind to a target nucleic acid sequence of interest. In some capture probes, the first segment is designed to bind to a segment within a particular target nucleic acid and not to (or at least with substantially reduced affinity) other nucleic acids lacking this segment that are present in the sample. In other capture probes, the first segment is designed to bind to a class of target nucleic acids (e.g., any DNA molecule) and does not necessarily substantially discriminate between individual target nucleic acids within the class (e.g., by use of a randomized sequence).

For the first segment to bind to a particular target nucleic acid sequence of interest, the first segment can be designed to include a nucleic acid that is substantially and preferably exactly complementary to a corresponding segment of the target nucleic acid. The nucleic acid of such a first segment preferably includes at least 6, 10, 15 or 20 nucleobase units (e.g., nucleotides). For example, the nucleic acid can contain 10-50, 10-40, 10-30 or 15-25 nucleobase units (e.g., nucleotides) complementary to corresponding nucleotides in the target nucleic acid. Here, as elsewhere in the application, ranges for contiguous nucleic acid sequences are fully inclusive of all whole numbers defining or within the range (10, 11, 12, 13 . . . 47, 48, 49, 50).

For a capture probe to capture a population of related target molecules (e.g., a viral RNA population in a patient sample in which molecules differ from one another by the presence of mutations), the capture probe is preferably designed to be complementary to a target segment that is relatively conserved among different members of the population.

For the first segment to bind nonspecifically to nucleic acids without necessarily substantially discriminating between different sequences within a class, the first segment can include a random polymer sequence made up of all four standard DNA bases (guanine (G), cytosine (C), adenine (A) and thymine (T)) or all four standard RNA bases (G, C, A, and uracil (U)) (see US 2008/0286775) The random sequence can also include one or more base analogs (e.g., inosine, 5-nitroindole) or abasic positions in the random polymer sequence. Such a random polymer sequence can contain one or more sequences of poly-(K) bases, i.e., a random mixture of G and U or T bases (e.g., see Table 1 of WIPO Handbook on Industrial Property Information and Documentation, Standard ST.25 (1998)). Sequences that include G and U/T bases can be chosen for their "wobble" property, i.e., U/T binds G or A, whereas G binds C or U/T. A capture probe having a first segment synthesized with a random polymer sequence is in fact a finite population of oligonucleotides that contain different random polymer sequences made up of the bases included during the synthesis of the random portion. For example, a population of nonspecific capture probes that include a 15 nt random polymer sequence made up of G, C, A and T consists of $4^{15}$ members. The first segment can be designed to bind to DNA sequences preferentially relative to RNA or vice versa (see US 2008-0286775).

The second segment is designed to bind to an immobilized probe. The second segment includes a nucleic acid that is substantially and preferably exactly complementary to a nucleic acid present in the immobilized probes. Optionally, the second segment of the immobilized probe and the complementary segment in the immobilized probe can both be L-nucleic acids, as described in a co-pending application PCT/US2011/052050. Because L-nucleic acids hybridize only to other L-nucleic acids, the use of L-nucleic acids can further increase the specificity of capture of a desired target nucleic acid. The nucleic acid of the capture probe preferably includes at least six nucleobase units (e.g., D or L-nucleotides) and preferably 10-50, 10-40, 10-10 or 15-25 nucleobase units. Ranges for contiguous nucleic acid sequences are fully inclusive of all whole numbers (10, 11, 12, 13 . . . 47, 48, 49, 50) defining or within the range. The L-nucleic acid of the capture probe is preferably a homopolymer and more preferably polyA and/or polyT (e.g. $d(T)_{0-5}/d(A)_{10-40}$, ranges being inclusive of all whole numbers defining or within the range). A preferred nucleic acid is or includes a homopolymer of 30 adenines. The length of the nucleic acid (i.e., number of nucleobase units) in the capture probe may or may not be the same as the length of the nucleic acid in the immobilized probe.

The melting temperature of the duplex formed between the nucleic acid of the capture probe and nucleic acid of the immobilized probe preferably has a lower melting temperature than the duplex formed between the nucleic acid of the first segment of the capture probe and the target nucleic acid. The melting temperatures of both duplexes can be calculated by conventional equations relating base composition and length of a duplex to its melting temperature as discussed above. Selection of polyA or polyT homopolymers for the nucleic acids of the capture and immobilized probes tends to confer a lower melting temperature than that for a duplex formed between the first segment of the capture probe and the target nucleic acid because the latter duplex usually also contains some C-G pairings, which confer greater stability on a duplex than A-T pairings. A lower melting temperature of the duplex formed between the second segment of the capture probe and the immobilized probe than the duplex formed between the first segment of the capture probe and the target nucleic acid is advantageous in allowing the hybridization to be performed under conditions of higher stringency in which the capture probe first hybridizes to the target nucleic acid and lower stringency in which the capture probe now hybridizes to the target nucleic acid hybridizes to the immobilized probe. When performed in this order, both capture probe and target nucleic acid are in solution when they hybridize in which conditions, hybridization takes place with much faster kinetics.

The capture probe may or may not include additional segments as well as the first and second segments mentioned above. For example, the nucleobase units of the first segment and nucleobase units of the second segment can be directly connected by a phosphodiester bond (or any of the analogs thereof discussed above) or can be separated by a short spacer or linker region, which may include nucleotides (D- or L), or other molecules, such as PEG typically found in linkers. For example, if the second segment is a polyA homopolymer, the first and second segments can be connected by one or more (e.g., three) thymine residues. A capture probes can also include a third segment such that the first segment is flanked by the second and third segments. In such an arrangement, the third segment can include a nucleic acid complementary to the nucleic acid in the second segment, such that the capture probe is capable of self-annealing to form a stem-loop structure in which the second and third segments are annealed as a stem and the first segment forms a loop in between. Such a stem loop structure can only form when the first target nucleic acid is not hybridized with its target nucleic acid. Such an arrangement can be useful in reducing the ability of a capture probe to hybridize with an immobilized probe before the capture probe has bound to its target nucleic acid and in reducing competition between unhybridized capture probe and a detection probe used to detect the target nucleic acid (see US 20060068417).

Multiple different capture probes can be used in combination in the same reaction. In this case, the different capture probes typically have different first segments complementary to different target nucleic acids or different segments within the same target nucleic acid, and the identical second segments, so they can bind immobilized probes having the complementary sequences to these second segments. Use of multiple different capture probes can be useful in capturing a population of related target sequences that may be present in a sample, for example, sequence and/or length variants. For example, in capturing a viral RNA population in which members differ from one another by presence of mutations, multiple capture probes binding to different conserved regions within the viral genome can be used. The number of different capture probes can be at least 1, 2, 5, 10, 20, 50 or 100, for example, 1-100 or 2-50 or 3-25, inclusive of all whole numbers defining or within the range.

The concentration of magnetic bead and capture probe used for target capture when the captured target is subsequently subjected to a real-time detection are typically less than an otherwise similar capture reaction subjected to an end-point detection. For example, the concentration of the capture probe in the present methods can be 0.2-0.8 pmol/ml or preferably 0.4-0.5 pmol/ml. Without being bound by any theory, it is believed higher levels of magnetic bead and capture probe interferes with the sensitivity of real-time detection more so than with the sensitivity of end-point detection.

IV. Immobilized Probe

An immobilized probe includes a nucleic acid joined directly or indirectly to a support. As indicated in the description of the capture probe, the nucleic acid is substantially or preferably exactly complementary to a nucleic acid in the capture probe, although may or may not be the same length (number of nucleobase units) as the nucleic acid in the capture probe. The complementary segments in the capture probe and immobilized probe are either both D-nucleic acids or both L-nucleic acids. The nucleic acid in the immobilized probe preferably contains at least six contiguous nucleobase units (e.g., D- or L-nucleotides) and can contain for example 10-45 or 10-40 or 10-30 or 10-25 or 15-25, inclusively, D- or L-nucleobase units, any range being inclusive of all whole numbers defining or within the range. The nucleic acid is preferably a homopolymer, and more preferably a homopolymer of adenine or thymine A preferred form of immobilized probe is or includes a homopolymer of 14 thymine residues for use in combination with a capture probe including a second segment with a homopolymer of adenine residues. The nucleic acid moiety of an immobilized probe is typically provided in single-stranded form, or if not, is denatured to single stranded form before or during use.

Any of a variety of materials may be used as a support for the immobilized probes, e.g., matrices or particles made of nitrocellulose, nylon, glass, polyacrylate, mixed polymers, polystyrene, silane polypropylene, and magnetically attractable materials. Monodisperse magnetic spheres are a preferred support because they are relatively uniform in size and readily retrieved from solution by applying a magnetic force to the reaction container, preferably in an automated system. An immobilized probe may be linked directly to the capture support, e.g., by using any of a variety of covalent linkages, chelation, or ionic interaction, or may be linked indirectly via one or more linkers joined to the support. The linker can include one or more nucleotides of either D or L-enantiomeric forms not intended to hybridize to the capture probe but to act as a spacer between the nucleic acid of the immobilized probe and its support. As mentioned above, the concentration of immobilized probe bound magnetic supports and capture probe used for target capture is typically less when target capture is coupled to a real-time detection than is the case for an end-point detection because higher concentrations of supports may inhibit the real-time detection sensitivity. For immobilized probe bound magnetic beads, the concentration is preferably 15-25 pg/ml, or about 20 pg/ml of the target capture reaction mix.

V. Target Nucleic Acid

A target nucleic acid refers to a nucleic acid molecule or population of related nucleic acid molecules that is or may be present within a sample. A target nucleic acid includes a segment (target segment) that hybridizes with the first segment on the capture probe to form a stable duplex. The target segment can be the same or substantially the same length as the nucleic acid of the first segment of the capture probe and exactly or substantially complementarity to this nucleic acid. The target segment can be only a small fraction of the total length of a target nucleic acid. For example, a target nucleic acid can be several thousand nucleotides long and a target segment can be for example, only 10-30 of these nucleotides. A target nucleic acid can exist in different forms, i.e., single-stranded, double-stranded, triple-stranded, or mixtures thereof, such as in a partially double-stranded hairpin structure or partially double-stranded duplex structure, and a target segment can present on any strand (sense or antisense) of the structure. A target nucleic acid can be RNA (e.g., viral RNA, micro RNA, mRNA, cRNA, rRNA, hnRNA or DNA (genomic or cDNA) among others. The target nucleic acid can be from a pathogenic microorganism, such as a virus, bacteria or fungus, or can be endogenous to a patient. A target nucleic acid can be synthetic or naturally occurring. A target nucleic acid can range in length from at least about ten nucleotides to more than 1000 nucleotides or up to 10,000 nucleotides or even greater than 10,000 nucleotides. Target nucleic acids having 25-10,000 nucleotides are common Viral nucleic acids (e.g., genomic, mRNA) form a useful target for analyses of viral sequences. Some examples of viruses that can be detected include HIV, hepatitis (A, B, or C), herpes virus (e.g., VZV, HSV-1, HAV-6, HSV-II, CMV, and Epstein Barr virus), adenovirus, XMRV, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, MLV-related Virus, papillomavirus, molluscum virus, poliovirus, rabies virus, JC virus and arboviral encephalitis virus.

Analysis of viral nucleic acids is particularly useful for analyzing drug resistance. Viruses mutate rapidly so that a patient is often infected with a heterogeneous population of viral nucleic acids, which changes over time. Some of the mutations differentiating species of the heterogeneous population may be associated with resistance to a drug that the patient has been treated with or may be treated with in the future. Deconvolution of the population to detect individual variants allows detection of drug resistant mutations and their change over time, thus allowing treatment regimes to be customized to take into account the drug resistance of strains infecting a particular patient. Because drug-resistant or other mutations may present as only a small proportion of viral nucleic acid molecules, sequencing of a large number of molecules in the viral nucleic population may be required to provide a high likelihood of identifying all drug resistant mutations or at least all, whose representation as a percentage of the total viral nucleic acid population exceeds a threshold. When the present methods of capturing and amplifying a target nucleic population are coupled to a massively parallel sequencing technique, at least 100,000, or 1,000,000 members of the target nucleic population can be sequenced. Using the present methods, it is possible to identify mutations present at representations of less than, for example, 10%, 1% or 0.1% can be identified. Read lengths of for example at least 100, 500, 1000, 2000, or 5000 nucleotides of target nucleic acid can be obtained.

Human nucleic acids are useful for diagnosing diseases or susceptibility towards disease (e.g., cancer gene fusions, BRACA-1 or BRAC-2, p53, CFTR, cytochromes P450), for genotyping (e.g., forensic identification, paternity testing, heterozygous carrier of a gene that acts when homozygous, HLA typing), determining drug efficacy on an individual (e.g., companion diagnostics) and other uses.

rRNA is particularly useful for detecting and/or typing pathogenic bacteria. Examples of such bacteria include chlamydia, rickettsial bacteria, mycobacteria, staphylococci, treptocci, pneumonococci, meningococci and conococci, *klebsiella, proteus, serratia, pseudomonas, legionella,* diphtheria, *salmonella,* bacilli, cholera, tetanus, botulism, anthrax, plague, leptospirosis, Lymes disease bacteria, streptococci, or *neisseria*.

VI. Sample

A "sample" or "biological sample" refers to any composition or mixture in which a target nucleic acid of interest may be present, including plant or animal materials, waste materials, materials for forensic analysis, environmental samples, and the like. A biological sample includes any tissue, cell, or extract derived from a living or dead organism which may contain a target nucleic acid, e.g., peripheral blood, bone marrow, plasma, serum, biopsy tissue including lymph nodes, respiratory tissue or exudates, gastrointestinal tissue, urine, feces, semen, or other body fluids. Samples of particular interest are tissue samples (including body fluids) from a human or an animal having or suspected of having a disease or condition, particularly infection by a virus. Other samples of interest include industrial samples, such as for water testing, food testing, contamination control, and the like.

Sample components may include target and non-target nucleic acids, and other materials such as salts, acids, bases, detergents, proteins, carbohydrates, lipids and other organic or inorganic materials.

A sample may or may not be subject of processing to purify or amplify a target nucleic acid before performing the target capture assay described below. It is not, for example, necessary to perform a column binding of elution of nucleic acids. Such a step concentrates and purifies nucleic acids but also can lose a large proportion of the sample. Further processing can include simple dilution of a biological fluid with a lysing solution to more complex (e.g., Su et al., J. Mol. Diagn. 2004, 6:101-107; Sambrook, J. et al., 1989, Molecular Cloning, A Laboratory Manual, 2nd ed., pp. 7.37-7.57; and U.S. Pat. Nos. 5,374,522, 5,386,024, 5,786, 208, 5,837,452, and 6,551,778). Viral RNA samples are often prepared by treating plasma or serum with detergent to release RNA from viruses. Typically, a sample containing a target nucleic acid is heated to inactivate enzymes in the sample and to make the nucleic acids in the sample single-stranded (e.g., 90-100° C. for 2-10 min, then rapidly cooling to 0-5° C.).

VII. Target Capture Assay

A target capture assay is performed using one or more chimeric capture probes, an immobilized probe, a sample and a suitable medium to permit hybridization of the capture probe to the target nucleic acid and of capture probe to the immobilized probe. Usually, the target sample is heated before performing the assay to denature any nucleic acids in double stranded form. The components can be mixed in any order. For example the capture probe can be added to the sample and hybridized with the target nucleic acid in the sample before adding the immobilized probe. Alternatively, the capture probe can already be hybridized to the immobilized probe before supplying these two probes to the assay mix. However, for an automated assay, it is preferable to minimize the number of adding steps by supplying the capture probe and immobilized probe at the same or substantially the same time. In this case, the order of hybridization can be controlled by performing a first hybridization under conditions in which a duplex can form between the capture probe and the target nucleic acid but which exceeds the melting temperature of the duplex that would form between the capture probe and immobilized probe, and then performing a second hybridization under conditions of reduced stringency. Stringency can most easily be reduced by lowering the temperature of the assay mix. For example, the higher stringency hybridization can be performed at or around 60° C. and the lower stringency hybridization by allowing cooling to room temperature.

Following formation of the target nucleic acid:capture probe: immobilized probe hybrid (the capture hybrid complex) is isolated away from other sample components by physically separating the capture support using any of a variety of known methods, e.g., centrifugation, filtration, or magnetic attraction of a magnetic capture support. To further facilitate isolation of the target nucleic acid from other sample components that adhere non-specifically to any portion of the capture hybrid, the capture hybrid may be washed one or more times to dilute and remove other sample components. Washing may be accomplished by dissociating the capture hybrid into its individual components in an appropriate aqueous solution (e.g., a solution containing Tris and EDTA. See e.g., U.S. Pat. No. 6,110,678) and appropriate conditions (e.g., temperature above the Tm of the components) and then re-adjusting the conditions to permit reformation of the capture hybrid. However, for ease of handling and minimization of steps, washing preferably rinses the intact capture hybrid attached to the capture support in a solution by using conditions that maintain the capture hybrid. Preferably, capture of the target nucleic acid with washing if performed, removes (that is, retains in the tube) at least 70%, preferably at least 90%, and more preferably about 95% of the target nucleic acid molecules from other sample components.

The target nucleic acid is then subject to PCR amplification, which in the case of RNA samples is an RT-PCR reaction, without prior release of the target nucleic acid from the capture complex. Although no step is performed with intent to dissociate the target nucleic acid from the capture probe before initiating PCR or RT-PCR, the target nucleic acid may be partially or completely dissociated from the capture probe in the course of thermocycling, particularly in a denaturation step performed at or around 95° C. The PCR reaction can be performed in the same vessel (e.g., a microfuge tube) as the capture step. The PCR reaction involves thermocycling between a high temperature of about 95 degrees (e.g., 90-99° C.) for dissociation and a low temperature of about 60° C. (e.g., 40-75, or 50-70 or 55-64°

C.) for annealing. Typically, the number of complete thermocycles is at least 10, 20, 30 or 40. PCR amplification is performed using one or more primer pairs. A primer pair used for PCR amplification includes two primers complementary to opposite strands of a target nucleic acid flanking the region desired to be sequenced. For sequencing most of a viral genome (e.g., more than 50, 75 or 99%), the primers are preferably located close to the ends of the viral genome. For amplification of related molecules (e.g., mutant forms of the same virus present in a patient sample), the primers are preferably complementary to conserved regions of the target nucleic acid likely to be present in most members of the population. (Depending on selection of primers, amplification does not necessarily amplify the entire length of a target nucleic acid, but in any case, the amplified product can still referred to as being amplified target nucleic acid.) PCR amplification is described in PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila et al., Nucleic Acids Res. 19, 4967 (1991); Eckert et al., PCR Methods and Applications 1, 17 (1991); PCR (eds. McPherson et al., IRL Press, Oxford); and U.S. Pat. No. 4,683,202.

Following PCR amplification, the amplified target can optionally be subject to further processing to purify it and/or modify it to be amenable to a particularly sequencing format. Purification if desired can be performed on a silica column (e.g., a Qiagen gravity flow column) The target nucleic acid binds to the column, where it can be washed and then eluted. The amplified target DNA can also be adapted for some sequencing formats by attachment of an adapter. The amplified DNA can be tailed by Klenow-mediated addition of nucleotides (usually a homopolymer) followed by annealing to an oligonucleotide complementary to the added tail, and ligation. Depending on the sequencing platform used, special adaptors are ligated to the template before sequencing. For example, a SMRT™ hairpin loop adapter can be ligated to the sample template for sequencing with a Pacific Biosciences' PacBio RS sequencer (see, e.g., Travers et al. Nucl. Acids Res. (2010) 38 (15): e159).

The amplified target nucleic acid is suitable for sequence analysis by a variety of techniques. (Depending on the primers used for amplification, the form of the template for sequencing and the sequencing technique, sequencing is not necessarily performed on the entire length of the originally captured target nucleic acid, but such sequencing can in any case be referred to as sequencing of the target nucleic acid or captured target nucleic acid.) The capture of target nucleic acid can be coupled to several different formats of so-called next generation and third generation sequencing methods. Such methods can sequence millions of target templates in parallel. Such methods are particularly useful when the target nucleic acid is a heterogeneous mixture of variants, such as is often the case in a sample from a patient infected with a virus, such as HIV. Among the many advantages, sequencing variants in parallel provides a profile of drug resistant mutations in the sample, even drug mutations present in relatively minor proportions within the sample.

Some next generation sequence methods amplify by emulsion PCR. A target nucleic acid immobilized to beads via a capture probe provides a suitable starting material for emulsion PCR. The beads are mixed with PCR reagents and emulsion oil to create individual micro reactors containing single beads (Margulies et al., Nature 437, 376-80 (2005)). The emulsion is then broken and the individual beads with amplified DNA are sequenced. The sequencing can be pyrosequencing performed for example using a Roche 454 GS FLX sequencer (454 Life Sciences, Branford, Conn. 06405). Alternatively, sequencing can be ligation/detection performed for example using an ABI SOLiD Sequencing System (Life Technologies, Carlsbad, Calif. 92008). In another variation, amplified target nucleic acids are immobilized in different locations on an array (e.g., the HiScanSQ (Illumina, San Diego, Calif. 92121)). The target nucleic acids are amplified by bridge amplification and sequenced by template directed incorporation of labeled nucleotides, in an array format (Illumina). In another approach, single molecules of amplified target nucleic acids are analyzed by detecting in real-time the incorporation of nucleotides by a polymerase (single-molecule real-time sequencing or SMRT™ sequencing). The nucleotides can be labeled nucleotides that release a signal when incorporated (e.g., Pacific Biosciences, Eid et al., Sciences 323 pp. 133-138 (2009) or unlabeled nucleotides, wherein the system measures a chemical change on incorporation (e.g., Ion Torrent Personal Genome Machine (Guilform, Conn. 94080)). In a preferred format, the target nucleic acids resulting from amplification are ligated to SMRT-bell™ adapters or otherwise converted to a circular template form and subjected to single-molecule real-time sequencing (Korlach et al., Nucleosides, Nucleotides and Nucleic Acids, 27:1072-1083 (2008), U.S. Pat. Nos. 7,181,122, 7,302,146, and 7,313, 308). In such a format, circular templates are sequenced individually and incorporated nucleobase unit is detected in real time before incorporation of the next incorporated nucleobase unit. Multiple passes around the template molecule can generate a sequencing read containing multiple copies of a target nucleic acid. Sequencing of an individual templates can take place in a cylindrical metallic chamber known as a zero mode waive guide, and many such individual templates each in its own zero mode waive guide can be sequenced in parallel.

Although captured target nucleic acids can be sequenced by any technique, third generation, next generation or massively parallel methods offer considerable advantages over Sanger and Maxam Gilbert sequencing. Several groups have described an ultra high-throughput DNA sequencing procedure (see. e.g., Cheeseman, U.S. Pat. No. 5,302,509, Metzker et al., Nucleic Acids Res. 22: 4259 (1994)). The pyrosequencing approach that employs four natural nucleotides (comprising a base of adenine (A), cytosine (C), guanine (G), or thymine (T)) and several other enzymes for sequencing DNA by synthesis is now widely used for mutation detection (Ronaghi, Science 281, 363 (1998); Binladin et al., PLoS ONE, issue 2, e197 (February 2007); Rehman et al., American Journal of Human Genetics, 86, 378 (March 2010); Lind et al., Hum. Immunol. 71:1033-42 (2010); Shafer et al., J. Infect Dis. 1; 199(5):610 (2009)). In this approach, the detection is based on the pyrophosphate (PPi) released during the DNA polymerase reaction, the quantitative conversion of pyrophosphate to adenosine triphosphate (ATP) by sulfurylase, and the subsequent production of visible light by firefly luciferase. More recent work performs DNA sequencing by a synthesis method mostly focused on a photocleavable chemical moiety that is linked to a fluorescent dye to cap the 3'-OH group of deoxynucleoside triphosphates (dNTPs) (Welch et al. Nucleosides and Nucleotides 18, 197 (1999) & European Journal, 5:951-960 (1999); Xu et al., U.S. Pat. No. 7,777,013; Williams et al., U.S. Pat. No. 7,645,596; Kao et al, U.S. Pat. No. 6,399,335; Nelson et al., U.S. Pat. Nos. 7,052,839 & 7,033,762; Kumar et al., U.S. Pat. No. 7,041,812; Sood et al, US Pat. App. No. 2004-0152119; Eid et al., Science 323, 133 (2009)). In sequencing-by-synthesis methodology, DNA sequences are being deduced by measuring pyrophosphate release on testing DNA/polymerase complexes with each deoxyribonucleotide triphosphate (dNTP) separately and sequentially. See Ronaghi et al., Science 281: 363 365 (1998); Hyman, Anal. Biochem. 174, 423 (1988); Harris, U.S. Pat. No. 7,767,400.

Sequencing platforms are further moving away from those that read a plurality of target nucleic acids towards single molecule sequencing systems. Amplification is desirable even for single molecule sequencing schemes because target nucleic acid can be used in preparing the template for sequencing. Earlier systems analyze target nucleic acids in bulk. What this means is that, for example with Sanger sequencing, a plurality of target nucleic acids are amplified in the presence of terminating ddNTPs. Collectively, each termination position read on a gel represents a plurality of amplification products that all terminated at the same nucleobase position. Single molecule sequencing systems use nanostructures wherein the synthesis of a complementary strand of nucleic acid from a single template is performed. These nanostructures are typically configured to perform reads of a plurality of single strand nucleic acids. Each single strand contributes sequence information to the sequence analysis system. See, Hardin et al., 7,329,492; Odera, US Pub. Pat. App No. 2003-0190647.

For a further review of some sequencing technologies, see Cheng, Biochem. Biophys. 22: 223 227 (1995); Mardis, Annual Review of Genomics and Human Genetics 9: 387-402 (2008) & Genome Medicine 1 (4): 40 (2009); Eid et al., Science 323, 133 (2009); Craighead et al., U.S. Pat. No. 7,316,796; Lipshutz, et al., Curr Opinion in Structural Biology, 4:376 (1994); Kapranov et al., Science 296, 916 (2002); Levene et al., U.S. Pat. No. 6,917,726, Korlach et al., U.S. Pat. No. 7,056,661; Levene et al. Science 299, 682 (2003); Flusberg et al., Nature Methods v. 7, no. 6, p. 461 (June 2010); Macevicz, U.S. Pat. Nos. 6,306,597 & 7,598,065; Balasubramanian et al., U.S. Pat. No. 7,232,656; Lapidus et al, U.S. Pat. No. 7,169,560; Rosenthal et al., U.S. Pat. No. 6,087,095; Lasken, Curr Opin Microbiol. 10(5):510 (2007); Ronaghi et al., Pharmacogenics. Volume 8, 1437-41 (2007); Keating et al., PLoS One 3(10):e3583 (2008); Pease et al., PNAS USA 91(11):5022 (1994); Lockhart, et al., Nat Biotechnol. 14(13):1675 (1996); Shendure et al., Science 309, 1728 (2005); Kim et al., Science 316, 1481 (2007); Valouev et al. Genome Research 18 (7): 1051 (2008); Cloonan et al., Nature Methods 5 (7): 613 (2008); Tang et al. Nature Methods 6 (5): 377 (2009); McKernan et al. Genome Research 19 (9): 1527 (2009); Ecker et al., Nature Reviews Microbiology 6, 553 (2008).

VI. Kits

The invention also provides kits for performing the methods for capturing and amplifying targets. Kits contain some and usually all of at least one capture probe, at least one immobilized probe, and at least one primer pair for PCR amplification as described above. In preferred kits, the immobilized probe is immobilized to a magnetized particle, preferably a paramagnetic bead, with homopolymeric oligomers (e.g., polyA, polyT, polyC, or polyG) attached to it that are complementary to a homopolymeric portion of the capture probe in the kit. Kits can also include chemical compounds used in forming the capture hybrid and/or detection hybrid, such as salts, buffers, chelating agents, and other inorganic or organic compounds. Kits can also include reverse transcriptase and a DNA polymerase for performing RT-PCR. Kits can also include one or more reagents for performing sequencing, such as SMRT™-bell (hairpin loop sequencing primer binding sites) or other oligonucleotides for generating a circular template, a sequencing primer, a sequencing polymerase, a set of nucleotides for incorporating in sequencing, optionally bearing different fluorescent labels. Kits can also include chemicals for preparing samples for use in the invention methods which may include individual components or mixtures of lysing agents for disrupting tissue or cellular material and preserving the integrity of nucleic acids. Such compositions include enzymes, detergents, chaotropic agents, chelating agents, salts, buffering agents, and other inorganic or organic compounds. Kits can include any combination of the capture probe, immobilize probe and primer pair components described above which can be packaged in combination with each other, either as a mixture or in individual containers. Kits can also contain instructions for performing the capture methods described above.

Although the invention has been described in detail for purposes of clarity of understanding, certain modifications may be practiced within the scope of the appended claims. All publications and patent documents cited in this application are hereby incorporated by reference in their entirety for all purposes to the same extent as if each were so individually denoted. To the extent difference sequences might be associated with the same accession number at different times, the sequence associated with the accession number at the effective filing date is meant. The effective filing date means the earliest priority date at which the accession number at issue is disclosed. Unless otherwise apparent from the context any element, embodiment, step, feature or aspect of the invention can be performed in combination with any other

EXAMPLES

Example 1

Capture Probe and Amplification Primers

An exemplary capture probe sequence for capture of HCV (SEQ ID NO:1) is the following: 5'-CCCGGGGCACTCG-CAAGCTT-TAAAAAAAAAAAAAAAAAAAAAAAAAAAAAA.

The part of this sequence complementary to HCV is 5'-CCCGGGGCACTCGCAAGC (SEQ ID NO:2). The remaining sequence is a homopolymer tail and a trinucleotide T linker.

Some exemplary primer pairs for amplification of HCV are as follows (Table 1):

TABLE 1

| SEQ ID NO: | Sequence 5' → 3' |
|---|---|
| SEQ ID NO: 3 | CTGCGGAACCGGTGAGTACACC |
| SEQ ID NO: 4 | CTCGCAAGCACCCTATCAGGCAGT |

TABLE 1-continued

| SEQ ID NO: | Sequence 5' → 3' |
|---|---|
| SEQ ID NO: 5 | CTAGCCATGGCGTTAGTATGAGTGTCGTGCAG |
| SEQ ID NO: 6 | AGGCATTGAGCGGGTTGATCCAAGAAAGGAC |
| SEQ ID NO: 7 | AACCCACTCTATGYCCGGYCAT. |
| SEQ ID NO: 8 | GAATCGCTGGGGTGACCG |
| SEQ ID NO: 9 | CCATGAATCACTCCCCTGTGAGGAACTA |
| SEQ ID NO: 10 | TTGCGGGGGCACGCCCAA |
| SEQ ID NO: 11 | GGGGCACTCGCAAGCACCCTATCAGGCAGTACC |
| SEQ ID NO: 12 | TCRTCCYGGCAATTCCGGTGTACTCACCGGTTC |
| SEQ ID NO: 13 | CTGCGGAACCGGTGAGTACACCG |
| SEQ ID NO: 14 | CTGCGGAACCGGTGAGTACACCGGAATTGCCAGG ACGA |
| SEQ ID NO: 15 | CTGCGGAACCGGTGA |
| SEQ ID NO: 16 | CTGCGGAACCGGTGAG |
| SEQ ID NO: 17 | CTGCGGAACCGGTGAGTA |
| SEQ ID NO: 18 | CTGCGGAACCGGTGAGTACA |
| SEQ ID NO: 19 | CTGCGGAACCGGTGAGTACACCGG |
| SEQ ID NO: 20 | CTGCGGAACCGGTGAGTACACCGGAA |
| SEQ ID NO: 21 | CTGCGGAACCGGTGAGTACACCGGAAT |
| SEQ ID NO: 22 | CTGCGGAACCGGTGAGTACACCGGAATT |
| SEQ ID NO: 23 | CTGCGGAACCGGTGAGTACACCGGAATTGCCA |
| SEQ ID NO: 24 | CTGCGGAACCGGTGAGTACACCGGAATTGCCAGGA |
| SEQ ID NO: 25 | CTGCGGAACCGGTGAGTACACCGGAATTGCCAGGA CGACCGGGT |
| SEQ ID NO: 26 | GGTACTGCCTGATAGGGTGCTTGCGAG |
| SEQ ID NO: 27 | TGGTACTGCCTGATAGGGTGCTTGCGAG |
| SEQ ID NO: 28 | TGTGGTACTGCCTGATAGGGTGCTTGCGAG |
| SEQ ID NO: 29 | TTGTGGTACTGCCTGATAGGGTGCTTGCGAG |
| SEQ ID NO: 30 | AGGCCTTGTGGTACTGCCTGATAGGGTGCTTGCGAG |
| SEQ ID NO: 31 | TACTGCCTGATAGGGTGCTTGCGAG |
| SEQ ID NO: 32 | KKKKKKKKKKKKKKKKKKTTTAAAAAAAAAAAAAA AAAAAAAAAAAAAAA |

Exemplary primer combinations include a forward primer from SEQ ID NOS:3 & 13-25 and a reverse primer from SEQ ID NOS:4, 11 & 26-31. The invention is not limited by these exemplary capture probe and primer sequences, which are provided merely to illustrate the invention. Similarly, the invention is not limited by the HCV target nucleic acid, also provided to illustrate the invention integrated capture and amplification.

Example 2

Integrated Capture and Amplification of HCV From Clinical Samples

This example performs an integrated capture and amplification of HCV from clinical samples to show that captured samples can be PCR amplified in the presence of magnetic beads. The clinical samples were selected to provide a mixture of HCV genotypes in a ratio that provided one of the genotypes as a substantially minority species in the mix. In one set of conditions, the samples were 90% HCV1a and 10% HCV3b. In a second set of conditions, the samples were 99% HCV1a+1% HCV3b. HCV RNA from these mixed population samples was captured and the 5' untranslated regions of each of the genomes were RT-PCR amplified in integrated reactions.

Reagents used in these experiments were SEQ ID NOS:1, 3 and 4; SYBR GREEN RT-PCR mix and enzyme (ABI); heat-inactivated HCV1a and HCV3b plasma; oligo d(T)14 magnetic beads and a Rotorgene 3000 (Qiagen). SEQ ID NO:1 was a target capture oligomer and SEQ ID NOS:3 and 4 are primers. Sample 1 was provided as 100% heat-inactivated HCV1a plasma at a concentration of 1.56E5 copies/mL. Sample 2 was provided as 100% HCV3b plasma at a concentration of 1.56E5 copies/mL. Sample 3 was provided as 90% heat inactivated HCV1a plasma and 10% HCV3b plasma (246.5 µL, of sample 1 and 103.5 µL of sample 2). Sample 4 was provided as 99% heat inactivated HCV1a plasma and 1% HCV3b plasma (337 µL of sample 1 and 13 µL, of sample 2).

Target captures were performed by combining 280 µL of target capture reagent per reaction with 350 µL of sample. Capture conditions were a 30 minute incubation at 60° C. followed by a 30 minute cool-down to 20° C. Following capture, washes were performed using 500 µL of wash buffer per reaction. The capture complexes (magnetic bead/immobilized probe:capture probe:target nucleic acid) were maintained during the wash steps; thus there was no target elution performed. Capture beads complexed to the various capture probe:target nucleic acids and were then transferred to wells of a PCR reaction tray and resuspended in 40 µL of the SYBR GREEN RT-PCR mix containing 0.9 mM each primer, enzyme and water to a final volume of 50 µL. A real time RT-PCR reaction was performed. Following the RT-PCR reaction, 10 microliters of each PCR reaction condition was run on a 2% gel. (FIG. 1) The amplification products were all about 170 base pairs in length. The amplification product was also prepared for sequencing using a Pacific Biosciences sequencer (PacBio RS, Pacific Biosciences, Menlo Park, Calif.) according to manufacturer's instructions (results not shown). Briefly, the amplified product was separated from other nucleic acids in the reaction mixture using a spin column (QIAGEN, Gaithersberg, Md.) and quantitated using a Qubit system (Invitrogen, Carlsbad, Calif.), each according to manufacturers' instructions. Qubit quantitative results were as follows: Sample 1: 340 ng/µl; Sample 2: 313 ng/µl; Sample 3: 296 ng/µl; and Sample 4: 356 ng/µl. The amplified product was then ligated with the appropriate amount of SMRT™Bell adapters (Pacific Biosciences), according to manufacturer's instructions. The amplification products generated from the integrated amplification and capture method in this example were then ready for sequencing.

These results show amplification of a target nucleic acid performed in an amplification reaction that is integrated with the target capture reaction containing magnetic capture beads. Amplification products were provided in robust amounts. The amplification products present as clean bands on a 2% gel at their appropriate sizes.

Example 3

Comparison of an Integrated Capture and Amplification Method to a Capture, Elution and Amplification Method This example compares integrated non-specific capture and amplification to non-specific capture, elution and amplification. The integrated capture and amplification method does not have an elution step, whereas the capture, elution and amplification method does have an elution step. Reagents were as follows:

Materials:

The target nucleic acid was heat-attenuated influenza virus A purchased from ZeptoMetrix (Buffalo N.Y., Cat #NATFLUAH1-ST). The concentration of stock virus was 7.47 e5 copies/μL. A serial dilution of stock was made to include concentrations of 250 copies/180 μL; 125 copies/180 μL; 62.5 copies/180 μL; 31.25 copies/180 μL; and 15.625 copies/180 μL.

The amplification and detection kit was a real-time PCR assay available from Gen-Probe Prodesse, Inc., (Waukesha, Wis., ProFlu+, 100rxns cat #H44VKOO, 1500rxns cat #H44VK77, Control Kit cat #H44VK55). The real-time PCR assay was performed generally according to manufacturer's instruction.

The non-specific target capture reagent used for the integrated capture and amplification method was a wobble capture oligonucleotide (SEQ ID NO:32) used as generally described herein. (See also US Pat App 2008/0286775 for capture using a K18 wobble oligonucleotide).

The non-specific target capture reagent used for the capture/elute/amplify method was the BioMerieux NucliSense® (Durham, N.C.) Magnetic Extraction Reagents (cat #200 293), Lysis Buffer (cat #200 292), NucliSense® MiniMAG® (cat #200 305). The capture and elution was performed according to manufacturer's instructions. MiniMAG® is a commercially available system in which nucleic acids bind nonspecifically to magnetic silica and are eluted from the magnetic silica before PCR amplification. In comparative testing, MiniMAG has been reported to give the highest yields of DNA among three commercial systems being compared. Tang et al., J. Clin. Microbiol. 43,4830-4833 (2005).

Methods:

A deep-well 96 well plate was prepared for each reaction condition. A first plate was prepared for the integrated capture and amplification of influenza virus A RNA. 180 μL of each serial dilution was combined in a well with 20 μL of internal control reagent from the ProFlu+ kit. 160 μL of target capture reagent containing SEQ ID NO:32 was then added to each of the wells for a total volume of 360 μL. The target capture reaction was performed as follows: the plate was incubated at 60° C. for 20 min and then at room temperature for 30 min; the plate was washed three times with wash buffer from a PROCLEIX® kit (Gen-Probe Incorporated, cat #1116) on a KingFisher 96 Instrument with 3 wash plates; the captured and washed target nucleic acids were then resuspended in 20 λL of a PCR MasterMix made according the ProFlu+ protocol, and the mixture was amplified in a PCR reaction using the RotorGene 3000 according to the ProFlu+ amplification protocol. For samples having influenza virus A, twelve replicates were assayed for each condition. For negative control six replicates were assayed.

A second plate was prepared to contain 180 μL of each serial dilution in a separate well. Influenza virus A RNA was captured from these separate conditions using the MiniMag according to manufacturer's instructions with the elution volume set at 30 μL. PCR was performed using 5 μL of the 30 microliter elution volume and using the ProFlu+ kit as described above.

Results:

The results of the PCR assay (Table 2) show that the integrated non-specific capture and amplification method provided cycle time (Ct) values that were lower and had less standard deviation than were the cycle time results obtained from the capture, elution and amplification method. In Table 2, columns A-D are detection results from integrated non-specific capture and amplification; columns A and B are results for influenza virus A target nucleic acids; columns C and D are results for internal controls; columns E-H are results for capture, elution and amplification; columns E and F are results for influenza virus A; and columns G and H are results for internal controls.

Figure 2:
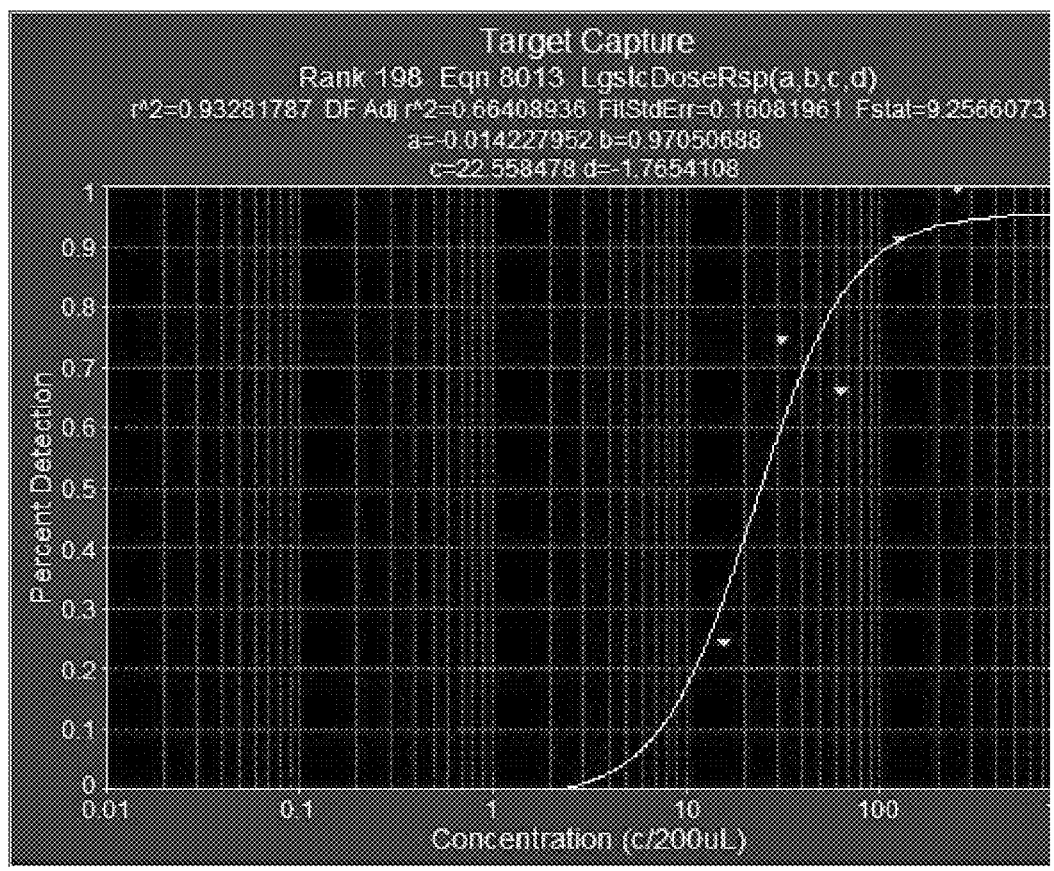
FIG. 2 is a detection limit graph illustrating 50% detection at 24 copies.
Figure 3:
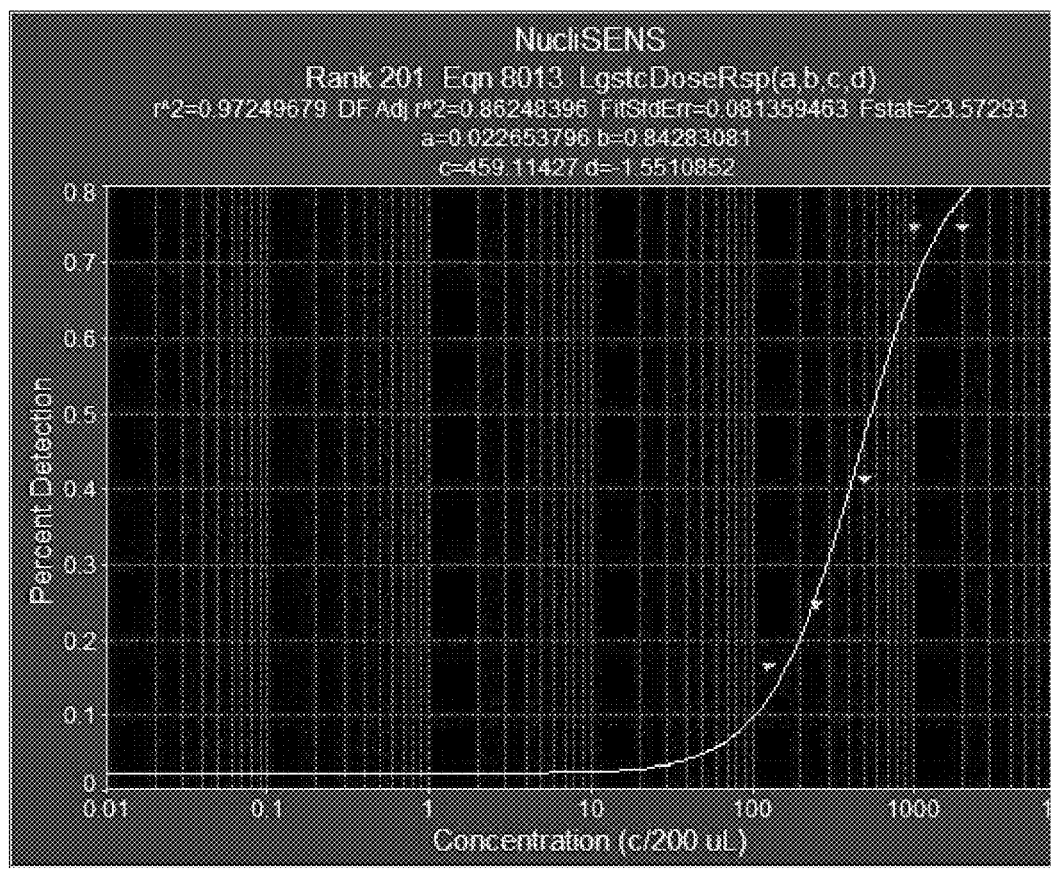
FIG. 3 is a detection limit graph illustrating 50% detection at 545 copies.

Setting a limit of detection at 50% (LOD), the integrated non-specific target capture and amplification method was far more sensitive than was the capture, elution and amplification method (FIGS. 2 and 3). The integrated method resulted in an LOD of 24 copies, whereas the non-integrated method resulted in an LOD of 545 copies. Thus, the integrated method is far more sensitive than is the non-integrated method.

TABLE 2

| Input copies of fluA | A Mean (Ct) (±SD) | B Percent Positive | C Mean (Ct) (±SD) | D Percent Positive | E Mean (Ct) (±SD) | F Percent Positive | G Mean (Ct) (±SD) | H Percent Positive |
|---|---|---|---|---|---|---|---|---|
| 250 | 31 (0.9) | 100 | 18.9 (0.3) | 100 | 36.3 (4.6) | 75 | 22.1 (0.9) | 100 |
| 125 | 31.5 (1.5) | 91.6 | 18.7 (0.3) | 100 | 37.9 (3.6) | 75 | 22.1 (1.1) | 100 |
| 62.5 | 33.1 (1.2) | 66.7 | 18.7 (0.2) | 100 | 38.7 (3.8) | 41.7 | 22.1 (0.9) | 100 |
| 31.25 | 33.2 (1.4) | 75 | 18.8 (0.2) | 100 | 36.9 (2.2) | 25 | 22.6 (0.7) | 100 |
| 15.625 | 34.3 (0.5) | 25 | 18.9 (0.3) | 100 | 36 (1.4) | 16.7 | 22.7 (0.6) | 100 |
| Flu A Positive Control | 28 (0.3) | 100 | N/A | 0 | 28.1 (0.5) | 100 | N/A | 0 |
| Negative Control | 0 (0) | 0 | 18.9 (0.3) | 100 | 0 (0) | 0 | 22.3 (1.3) | 100 |

CONCLUSION

The integrated non-specific target capture and amplification method allowed for the direct amplification/detection of captured Flu A RNA without an additional elution step resulting in superior sensitivity and lower Ct values compared to a non-hybridization-based nucleic acid capture, elution and amplification method, which requires the elution step.

What is claimed is:

1. A method of preparing a target nucleic acid, comprising contacting a target nucleic acid with a capture probe and an immobilized probe, the capture probe comprising a first segment that binds to the target nucleic acid and a second segment that binds to the immobilized probe, wherein the target nucleic acid binds to the first segment of the capture probe, and the second segment of the capture probe binds to the immobilized probe, thereby forming a capture hybrid capturing the target nucleic acid; and performing a PCR amplification with real time detection of the captured target nucleic acid without a step of dissociating the capture hybrid before initiating thermocycling in the PCR amplification; wherein the PCR amplification is performed in the same vessel as the contacting step.

2. The method of claim 1, wherein the target nucleic acid is an RNA molecule and the PCR amplification is an RT-PCR amplification.

3. The method of claim 2, wherein the target nucleic acid is a viral RNA population.

4. The method of claim 1, wherein the immobilized probe is immobilized via attachment to a magnetic bead.

5. The method of claim 4, wherein the concentration of immobilized probe linked to magnetic beads is 10-30 pg/ml.

6. The method of claim 1, wherein the PCR involves thermocycling between temperature ranges of 90-99° C., and 55-65° C.

7. The method of claim 1, wherein the concentration of the capture probe is 0.2-0.8 pmol/ml.

8. The method of claim 1, wherein the target nucleic acid is present in a serum or plasma sample.

9. The method of claim 8, wherein the serum or plasma sample is treated with detergent to release viral RNA.

10. The method of claim 1, wherein the first segment includes a nucleic acid of 10-30 bases complementary to the target nucleic acid.

11. The method of claim 3, wherein the contacting is performed with a plurality of capture probes, the capture probes having the same second segment and different first segments, the different first segments being complementary to different conserved regions of a viral RNA target.

12. The method of claim 1, wherein the first segment includes a random sequence of nucleotides that binds non-specifically to the target nucleic acid.

13. The method of claim 12, wherein the second segment includes a nucleic acid of 10-30 bases complementary to a nucleic acid of 10-30 contiguous bases in the immobilized probe.

14. The method of claim 13, wherein the nucleic acid of the second segment is a homopolymer and the nucleic acid of the immobilized probe constitute a complementary homopolymer.

15. The method of claim 14, wherein the homopolymer of the second segment is poly-A and the homopolymer of the immobilized probed is poly-T or vice versa.

16. The method of claim 12, wherein the second segment of the capture probe and the complementary segment of the immobilized probe are L-nucleic acids.

17. The method of claim 1, wherein the target nucleic acid is contacted with the capture probe and immobilized probe simultaneously.

18. The method of claim 1, wherein the binding of the target nucleic acid to the capture probe occurs under first hybridization conditions and the binding of the capture probe to the immobilized probe occurs under second hybridization conditions and the first conditions are more stringent than the second conditions.

19. The method of claim 18, wherein the first conditions are at a higher temperature than the second conditions.

20. The method of claim 18, wherein the first conditions include a temperature of 50-70° C. and the second conditions include room temperature.

* * * * *

SEQUENCE LISTING

<160> NUMBER OF SEQ ID NOS: 35

<210> SEQ ID NO 1
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 1
cccggggcac tcgcaagctt taaaaaaaaa aaaaaaaaaa aaaaaaaaaa a          51

<210> SEQ ID NO 2
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
cccggggcac tcgcaagc                                              18

<210> SEQ ID NO 3
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 3
ctgcggaacc ggtgagtaca cc                                         22

<210> SEQ ID NO 4
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 4
ctcgcaagca ccctatcagg cagt                                       24

<210> SEQ ID NO 5
<211> LENGTH: 32
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 5
ctagccatgg cgttagtatg agtgtcgtgc ag                              32

<210> SEQ ID NO 6
<211> LENGTH: 31
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic primer"

<400> SEQUENCE: 6
aggcattgag cgggttgatc caagaaagga c                                    31

<210> SEQ ID NO 7
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 7
aacccactct atgyccggyc at                                              22

<210> SEQ ID NO 8
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 8
gaatcgctgg ggtgaccg                                                   18

<210> SEQ ID NO 9
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 9
ccatgaatca ctcccctgtg aggaacta                                        28

<210> SEQ ID NO 10
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 10
ttgcgggggc acgcccaa                                                   18

<210> SEQ ID NO 11
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 11
ggggcactcg caagcaccct atcaggcagt acc                                  33

<210> SEQ ID NO 12
```

<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 12
tcrtccyggc aattccggtg tactcaccgg ttc         33

<210> SEQ ID NO 13
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 13
ctgcggaacc ggtgagtaca ccg         23

<210> SEQ ID NO 14
<211> LENGTH: 38
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 14
ctgcggaacc ggtgagtaca ccggaattgc caggacga         38

<210> SEQ ID NO 15
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 15
ctgcggaacc ggtga         15

<210> SEQ ID NO 16
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 16
ctgcggaacc ggtgag         16

<210> SEQ ID NO 17
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 17

-continued ctgcggaacc ggtgagta                                          18

<210> SEQ ID NO 18
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 18
ctgcggaacc ggtgagtaca                                        20

<210> SEQ ID NO 19
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 19
ctgcggaacc ggtgagtaca ccgg                                   24

<210> SEQ ID NO 20
<211> LENGTH: 26
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 20
ctgcggaacc ggtgagtaca ccggaa                                 26

<210> SEQ ID NO 21
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
ctgcggaacc ggtgagtaca ccggaat                                27

<210> SEQ ID NO 22
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 22
ctgcggaacc ggtgagtaca ccggaatt                               28

<210> SEQ ID NO 23
<211> LENGTH: 32
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic primer"

<400> SEQUENCE: 23
ctgcggaacc ggtgagtaca ccggaattgc ca                                      32

<210> SEQ ID NO 24
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 24
ctgcggaacc ggtgagtaca ccggaattgc cagga                                   35

<210> SEQ ID NO 25
<211> LENGTH: 44
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 25
ctgcggaacc ggtgagtaca ccggaattgc caggacgacc gggt                         44

<210> SEQ ID NO 26
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 26
ggtactgcct gatagggtgc ttgcgag                                            27

<210> SEQ ID NO 27
<211> LENGTH: 28
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
tggtactgcc tgatagggtg cttgcgag                                           28

<210> SEQ ID NO 28
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
tgtggtactg cctgatuggg tgcttgcgag                                         30
```

Note: Reading "tgtggtactg cctgataggg tgcttgcgag"

```
<210> SEQ ID NO 29
<211> LENGTH: 31
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 29
ttgtggtact gcctgatagg gtgcttgcga g                                  31

<210> SEQ ID NO 30
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 30
aggccttgtg gtactgcctg atagggtgct tgcgag                             36

<210> SEQ ID NO 31
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31
tactgcctga tagggtgctt gcgag                                         25

<210> SEQ ID NO 32
<211> LENGTH: 51
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 32
kkkkkkkkkk kkkkkkkktt taaaaaaaaa aaaaaaaaaa aaaaaaaaaa a            51

<210> SEQ ID NO 33
<211> LENGTH: 40
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"
<220> FEATURE:
<221> NAME/KEY: misc_feature
<222> LOCATION: (1)..(40)
<223> OTHER INFORMATION: /note="This sequence may encompass 10-40
      nucleotides"

<400> SEQUENCE: 33
aaaaaaaaaa aaaaaaaaaa aaaaaaaaaa aaaaaaaaaa                         40

<210> SEQ ID NO 34
<211> LENGTH: 30
<212> TYPE: DNA
<213> ORGANISM: Artificial Sequence
```

```
<220> FEATURE:
<221> NAME/KEY: source
<223> OTHER INFORMATION: /note="Description of Artificial Sequence:
      Synthetic probe"

<400> SEQUENCE: 34
aaaaaaaaaa aaaaaaaaaa aaaaaaaaaa                                          30

<210> SEQ ID NO 35
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
tttttttttt tttt                                                           14
```